US009320714B2

(12) United States Patent
Koike et al.

(10) Patent No.: US 9,320,714 B2
(45) Date of Patent: Apr. 26, 2016

(54) TABLET

(75) Inventors: Masahiko Koike, Osaka (JP); Hiroyoshi Koyama, Osaka (JP)

(73) Assignee: TAKEDA PHARMACEUTICAL COMPANY LIMITED, Osaka-Shi (JP)

( * ) Notice: Subject to any disclaimer, the term of this patent is extended or adjusted under 35 U.S.C. 154(b) by 1041 days.

(21) Appl. No.: 13/082,890

(22) Filed: Apr. 8, 2011

(65) Prior Publication Data

US 2011/0189282 A1 Aug. 4, 2011

Related U.S. Application Data

(63) Continuation of application No. 11/909,408, filed as application No. PCT/JP2006/306645 on Mar. 30, 2006.

(30) Foreign Application Priority Data

Mar. 31, 2005 (JP) .................................. 2005-102578

(51) Int. Cl.
*A61K 9/28* (2006.01)
*A61K 9/20* (2006.01)

(52) U.S. Cl.
CPC ................................... *A61K 9/2072* (2013.01)

(58) Field of Classification Search
CPC ............................... A61K 9/20; A61K 9/2072
USPC ........................................................ 424/474
See application file for complete search history.

(56) References Cited

U.S. PATENT DOCUMENTS

| 4,644,031 | A | * | 2/1987 | Lehmann et al. ............. 524/501 |
| 5,431,918 | A | | 7/1995 | Ferrero et al. |
| 5,770,225 | A | | 6/1998 | Parekh et al. |
| 6,589,925 | B1 | | 7/2003 | Binstock et al. |

(Continued)

FOREIGN PATENT DOCUMENTS

| JP | 2002-504112 | 2/2002 |
| JP | 2003-506415 | 2/2003 |

(Continued)

OTHER PUBLICATIONS

Ansel et al.: Pharmaceutical Dosage Forms and Drug Delivery Systems, 7th Edition, 1999, Lippincott Williams & Wilkins.*

(Continued)

*Primary Examiner* — Ernst V Arnold
*Assistant Examiner* — Hong Yu
(74) *Attorney, Agent, or Firm* — Rankin, Hill & Clark LLP (57) ABSTRACT

The present invention can retain the volume of a tablet large without increasing the thickness of the tablet or the like dimension and prevents a plurality of tablets from sticking to each other even if they are subjected to a film-coating or the like treatment, so as to improve the yield. The tablet is a tablet (1) longer in one direction when seen in plan. The tablet (1) has side edges (6) each of which extends in a longitudinal direction and is formed in the shape of a curve projecting outwardly in plan view. The curve has a radius of curvature (R1) set to at least 1.5 times a length (L) of the tablet. This makes a projected area of the tablet (1) in plan view at least 97% with respect to a projected area of a standard elliptical tablet having opposite end portions each of which is formed by a semi-circle having a diameter of a width (W) of the tablet.

7 Claims, 3 Drawing Sheets

TABLE OF COMPARISON OF DIMENSION

| | Tablet Length | Tablet Width | Radius of Curvature of Side Edge | Ratio of Radius of Curvature of Side Edge to Tablet Length | Radius of Curvature of End Arc | Projected Area in Top View | Projected Area Ratio to Standard Ellipse | Projected Area Ratio of Tablet Length and Width to Ellipse |
|---|---|---|---|---|---|---|---|---|
| | (mm) | (mm) | (mm) | (times) | (mm) | (mm²) | (%) | (%) |
| Example 1 | 18.5 | 10.0 | 111.00 | 6.00 | 4.91 | 162.0617 | 99.1 | 87.6 |
| Example 2 | 18.5 | 10.0 | 83.25 | 4.50 | 4.88 | 161.5265 | 98.8 | 87.3 |
| Example 3 | 18.5 | 10.0 | 74.00 | 4.00 | 4.86 | 161.2501 | 98.6 | 87.2 |
| Example 4 | 18.5 | 10.0 | 46.88 | 2.53 | 4.76 | 159.7085 | 97.7 | 86.3 |
| Example 5 | 18.5 | 10.0 | 41.63 | 2.25 | 4.72 | 159.1345 | 97.3 | 86.0 |
| Example 6 | 17.5 | 9.5 | 46.00 | 2.63 | 4.60 | 145.2734 | 98.9 | 87.4 |
| Example 7 | 13.5 | 8.5 | 46.00 | 3.41 | 4.20 | 98.8138 | 99.7 | 86.1 |
| Comparison Example 1 | 18.5 | 10.0 | -- | -- | 5.00 | 183.5398 | 100.0 | 88.4 |
| Comparison Example 2 | 17.5 | 9.5 | -- | -- | 4.75 | 146.8822 | 100.0 | 88.4 |
| Comparison Example 3 | 13.5 | 8.5 | -- | -- | 4.25 | 99.2450 | 100.0 | 86.5 |
| Comparison Example 4 | 16.0 | 8.5 | 15.00 | 0.94 | 3.25 | 109.4838 | 90.9 | 80.5 |
| Comparison Example 5 | 19.0 | 9.1 | 23.07 | 1.22 | 3.68 | 143.2720 | 92.1 | 82.6 |

(56) References Cited

U.S. PATENT DOCUMENTS

| | | |
|---|---|---|
| 6,635,282 B1 | 10/2003 | Flanagan et al. |
| 6,964,779 B1 | 11/2005 | Hayakawa et al. |
| 2003/0005800 A1 | 1/2003 | Czarnek et al. |

FOREIGN PATENT DOCUMENTS

| | | | |
|---|---|---|---|
| WO | 98/56360 | 12/1998 | |
| WO | 99/51207 | 10/1999 | |
| WO | 99/52491 | 10/1999 | |
| WO | 01/10464 | 2/2001 | |
| WO | WO 01/10464 A1 * | 2/2001 | ............. A61K 47/00 |

OTHER PUBLICATIONS

Osol: Remington's Pharmaceutical Science, Mack Publishing company, Easton, Pennsylvania 18042, 1980.*

Definition of Ellipse: retrieved from internet: http://mysite.du.edu/~jcalvert/math/ellipse.htm. Retrieved on May 18, 2015.*

* cited by examiner

Fig. 3    TABLE OF COMPARISON OF DIMENSION

| | Tablet Length (mm) | Tablet Width (mm) | Radius of Curvature of Side Edge (mm) | Ratio of Radius of Curvature of Side Edge to Tablet Length (times) | Radius of Curvature of End Arc (mm) | Projected Area in Top View (mm$^2$) | Projected Area Ratio to Standard Ellipse (%) | Projected Area Ratio of Tablet Length and Width to Ellipse (%) |
|---|---|---|---|---|---|---|---|---|
| Example 1 | 18.5 | 10.0 | 111.00 | 6.00 | 4.91 | 162.0617 | 99.1 | 87.6 |
| Example 2 | 18.5 | 10.0 | 83.25 | 4.50 | 4.88 | 161.5265 | 98.8 | 87.3 |
| Example 3 | 18.5 | 10.0 | 74.00 | 4.00 | 4.86 | 161.2501 | 98.6 | 87.2 |
| Example 4 | 18.5 | 10.0 | 46.88 | 2.53 | 4.76 | 159.7085 | 97.7 | 86.3 |
| Example 5 | 18.5 | 10.0 | 41.63 | 2.25 | 4.72 | 159.1345 | 97.3 | 86.0 |
| Example 6 | 17.5 | 9.5 | 46.00 | 2.63 | 4.60 | 145.2734 | 98.9 | 87.4 |
| Example 7 | 13.5 | 8.5 | 46.00 | 3.41 | 4.20 | 98.8138 | 99.7 | 86.1 |
| Comparison Example 1 | 18.5 | 10.0 | — | — | 5.00 | 183.5398 | 100.0 | 88.4 |
| Comparison Example 2 | 17.5 | 9.5 | — | — | 4.75 | 146.8822 | 100.0 | 88.4 |
| Comparison Example 3 | 13.5 | 8.5 | — | — | 4.25 | 99.2450 | 100.0 | 86.5 |
| Comparison Example 4 | 16.0 | 8.5 | 15.00 | 0.94 | 3.25 | 109.4838 | 90.9 | 80.5 |
| Comparison Example 5 | 19.0 | 9.1 | 23.07 | 1.22 | 3.68 | 143.2720 | 92.1 | 82.6 |

TABLET

CROSS-REFERENCE TO RELATED APPLICATIONS

This application is a continuation of co-pending application Ser. No. 11/909,408, filed Sep. 21, 2007, which is a U.S. national stage of PCT/JP2006/306645, filed Mar. 30, 2006, and claims priority to JP 2005-102578, filed Mar. 31, 2005.

TECHNICAL FIELD

The present invention relates to a tablet which is longer in one direction when seen in plan and more particularly to a tablet whose volume can be retained large without increasing its thickness or the like dimension and also whose yield can be improved by preventing them from sticking to each other even if they are subjected to a film-coating or the like treatment.

BACKGROUND ART

Figure 4A:
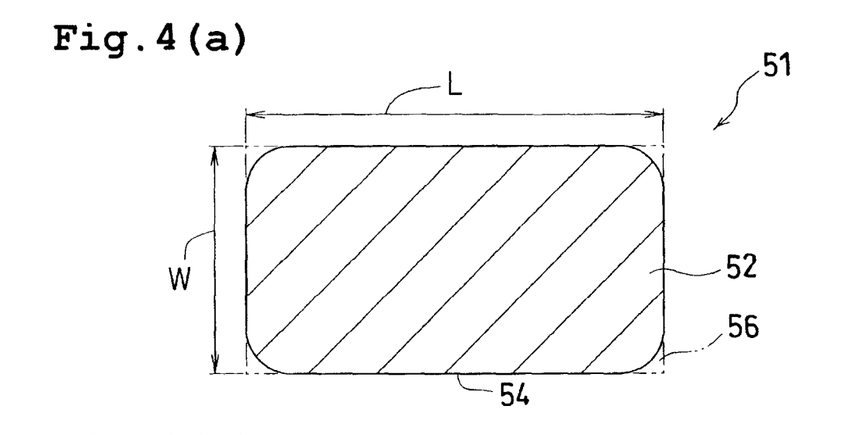
FIG. 4(a) is a top view, in cross section, of a substantially rectangular tablet having smooth corners.
Figure 4B:
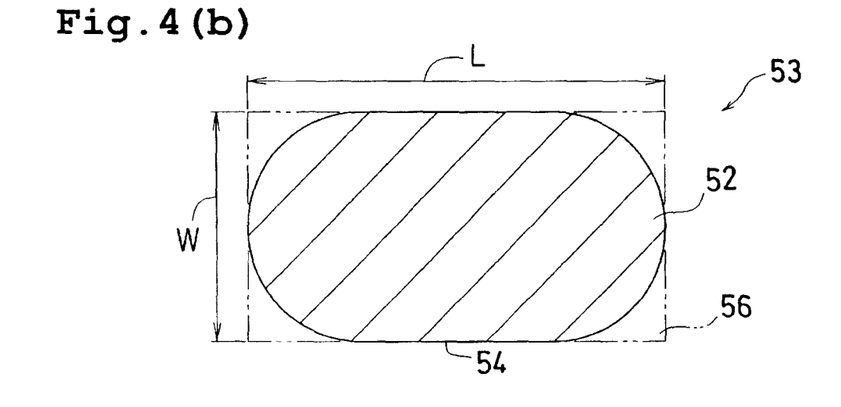
FIG. 4(b) is a top view, in cross section, of a standard elliptical tablet when seen in plan view.

There are known various shapes of tablets. One of them is a tablet which is longer in one direction when seen in plan (for example, see Patent Literature 1). Concrete examples of them are a substantially rectangular tablet (51) having smooth corners when seen in plan as shown in FIG. 4(a), a standard elliptical tablet (53) having its both ends (52) formed by semi-circles each of which has a diameter of a tablet width (W) when seen in plan as shown in FIG. 4(b) and a substantially oval tablet (55) having its side edges (54) each formed in the shape of a smooth arc (hereafter referred to as an 'oval tablet').

Figure 4C:
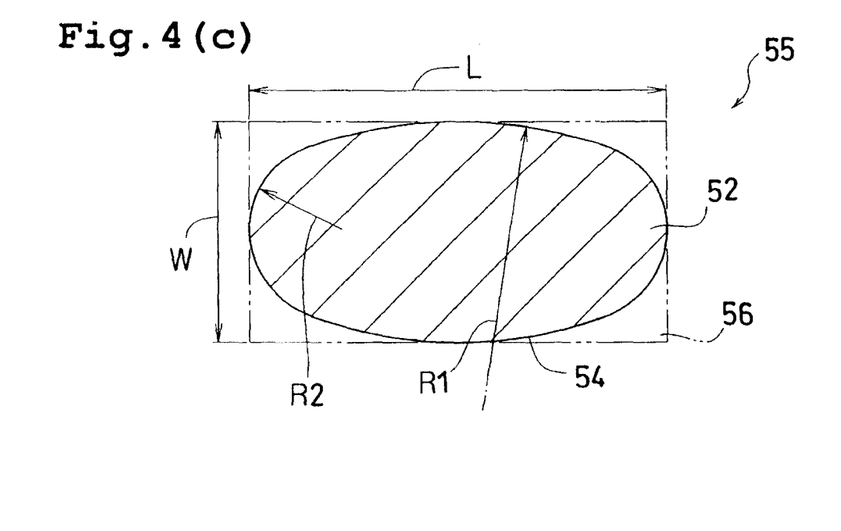
FIG. 4(c) is a top view, in cross section, of a substantially oval tablet.

Among them, the oval tablet (55) has a side edge (54) formed by an arc having a radius (R1), for example, about 1.5 times a tablet length (L), to which an end arc having a further smaller radius (R2) is connected smoothly so as to form an end portion (52). This oval tablet (55) has only a projected area of about 80% when compared with a rectangular tablet (56) having a width (W) and a length (L) (see FIG. 4(c)). So in order to keep the volume of this oval tablet large, it is necessary, for example, to increase the thickness of the tablet when compared with the standard elliptical tablet (53). However, there was a problem that if the thickness of the tablet is increased, the tablet could hardly be swallowed when it was dosed.

On the other hand, as for the substantially rectangular tablet (51) and the elliptical tablet (53) when seen in plan, the projected area is large in plan view. For example, in the case of the standard elliptical tablet (53), usually, the projected area is about 86% to 90% with respect to the rectangular tablet (56) (see FIG. 4(b)) having the width (W) and the length (L), although it may be different depending on the ratio of the width to the length. Further, as to the substantially rectangular tablet (51) when seen in plan, apparently, the ratio of its projected area is much higher. Thus as for these tablets, it is possible to easily retain the volume large without increasing the thickness of the tablet and the like dimension.

However, each of these substantially rectangular tablet (51) and the elliptical tablet (53) has a long linear portion at a side edge (54) in plan view, so that when it is subjected to the film-coating treatment, the long linear portion of this side edge (54) sticks to the other tablet through a coating agent to produce a so-called "twinning" defective product (hereafter referred to as "twin tablet"), which entails a problem of being not easy to improve the yield. Here, the twinning defective product also includes a defective product comprising at least three tablets mutually stuck.

Patent Literature 1: Utility Model Application Laid-Open No. 5-37924

DISCLOSURE OF THE INVENTION

The Problem the Invention Intends to Solve

The present invention has a technical object to solve the above-mentioned problems and provide a tablet which keeps its volume large without increasing its thickness or the like dimension and to enhance the yield by preventing a plurality of tablets from sticking to each other even if they are subjected to the film-coating or the like treatment.

Means for Solving the Problem

The present invention is constructed as follows so as to accomplish the above-mentioned object, for example, if it is explained based on FIGS. 1 to 3 which show embodiments of the present invention.

More specifically, a first invention 1 concerns a tablet longer in one direction, when seen in plan, which has a side edge 6 along a longitudinal direction formed by a curve projecting outwards when seen in plan view and has a projected area in plan view of at least 97% with respect to that of a standard elliptical tablet having both ends each of which is formed by a semi-circle having a diameter of a tablet width (W).

Further, a second invention 2 relates to a tablet longer in one direction when seen in plan and having a side edge 6 along the longitudinal direction, formed by a curve projecting outwards when seen in plan view. The side edge 6 has a radius of curvature (R1) at least 1.5 times a tablet length (L).

Hereafter, in the specification, the tablet of the first invention 1 and the tablet of the second invention 2 may be sometimes briefly referred to only as "the tablet of the present invention".

Here, the tablet may have ends formed mostly by straight lines like the substantial rectangle having round corners when seen in plan view or formed by one or plural arcs in combination like the substantial ellipse when seen in plan.

The aforesaid ratio of the projected area (hereafter referred to only as "projected area ratio") of this tablet when seen in plan view to the projected area of the standard elliptical tablet differs depending on not only the shape of the tablet end portion, but also the ratio of the tablet width to the tablet length and the radius of curvature of the side edge. As the radius of curvature of the side edge is larger, the projected area ratio can become larger.

As for the tablet of the present invention, its length is preferably set to about 1.5 to 2 times the tablet width from the aspect of the readiness and quantity of dosing. In this case, if the radius of curvature of the side edge is at least 1.5 times the tablet length, the projected area ratio can be easily set to at least 97%. So this is preferable. If it is at least two times the tablet length, the projected area ratio can become larger more assuredly. This is more preferable.

However, should the radius of curvature be excessively large, the arc of the side edge comes to readily butt against the side edge of the adjacent tablet over a long range when it is subjected to the film-coating treatment. As a result, there is a likelihood of twinning. Therefore, the radius of curvature is preferably set to not more than 6 times, preferably not more than 4.5 times, more preferably not more than 4 times the tablet length.

As regards a periphery of the tablet when seen in plan view, for example, the opposite end portions may be partly linear. But if whole the periphery is formed by curves projecting outwards in plan view, it is more preferable because there is no likelihood that the tablets stick to each other at any portion when it is subjected to the film-coating treatment.

In this case, the longitudinal ends of the tablet may be formed by large and small arcs in combination to which side edges extending along the longitudinal direction may be connected smoothly. However, if each of the end portions of this tablet is formed by an end arc having a single radius of curvature in plan view, both ends of which end arc are smoothly connected to the side edges along the longitudinal direction, the shape of the tablet is so simplified that the working becomes easy and besides the tablet-making pressure is readily applied to the tablet uniformly. Thus this is more preferable. Further, although the end arcs advantageously have their both ends connected to the side edges in contact relationship, it suffices if they are substantially smoothly connected thereto. Therefore, they may be connected together with a slight crossing angle.

The tablet of the present invention is suitably applied to the pharmaceutical medicine including pharmaceutical active components to be dosed in a large quantity or a plurality of pharmaceutical active components.

Here, listed as the pharmaceutical active components to be dosed in a large quantity, are, for example, metoformin or its salts (for example, hydrochloride), cefotiam hexetil hydrochloride, azithromycin hydrate, valaciclovir hydrochloride, and gabapentin.

Besides, listed as the plurality of pharmaceutical active components are, for example, a plurality of therapeutic agents for diabetes which provide mutually different effects and functions. Concretely, a combination of metoformin or its salts (for example, hydrochloride) with pioglytazon or its salts (for example, hydrochloride) is listed.

The tablet of the present invention weights at least 150 mg, preferably at least 300 mg, more preferably at least 600 mg. The upper limit is within a range where the tablet can be swallowed when it is dosed. Particularly, in the case where the tablet of the present invention weights at least 300 mg, the effect of the present invention, to be mentioned later, that the volume of the tablet can be kept large without increasing the thickness of the tablet or the like dimension will be exerted extraordinarily.

The tablet of the present invention is preferably a film-coated tablet having a film-coating layer from the view point of being easy to dose and well resistant to sun light, being able to make a good release control and having a sufficient hardness for pharmaceutical.

Here, the film-coating layer is generally 10 to 200 μm in thickness. This film-coating layer preferably contains a coating substrate (for example, hydroxypropylmethyl cellulose, hydroxypropyl cellulose, cellulose acetate, ethyl cellulose, methacrylic acid copolymer LD); in addition, a sunscreen agent such as titanium oxide, talc, 3,2 iron oxide; and a plasticizer such as polyethylene glycol, propylene glycol, polysolvate, triethyl citrate, triacetyne.

In the case where the tablet of the present invention is a film-coated tablet, the effect of the present invention [possibility of preventing a plurality of tablets from sticking to each other] to be mentioned later is extraordinarily exerted.

Effect of the Invention

Since the present invention is constituted and functions as mentioned above, it offers the following effects.

The first invention has a projected area in plan view set to at least 97% with respect to the projected area of the standard elliptical tablet. Further, the second invention has a projected area ratio increased by setting the radius of curvature of the side edge to at least 1.5 times the tablet length to result in being able to keep the volume large without augmenting the thickness of the tablet and the like dimension.

Having a side edge in the shape of a curve outwardly projecting, the tablet does not butt against the adjacent tablet over a long range. Accordingly, even if it is subjected to the film-coating or the like treatment, it is possible to prevent a plurality of tablets from sticking to each other with the result of being able to easily improve the yield

BRIEF DESCRIPTION OF THE DRAWINGS

[FIG. 4] shows conventional tablets.

EXPLANATION OF NUMERALS

1 . . . tablet
6 . . . side edge
7 . . . end portion
8 . . . end arc
L . . . length of the tablet
R1 . . . radius of curvature of the side edge (6)
R2 . . . radius of curvature of the end arc (8)
W . . . width of the tablet Most Preferred Embodiment of the Invention Hereafter, an explanation is given for the embodiments of the present invention based on the drawings.

Figure 1:
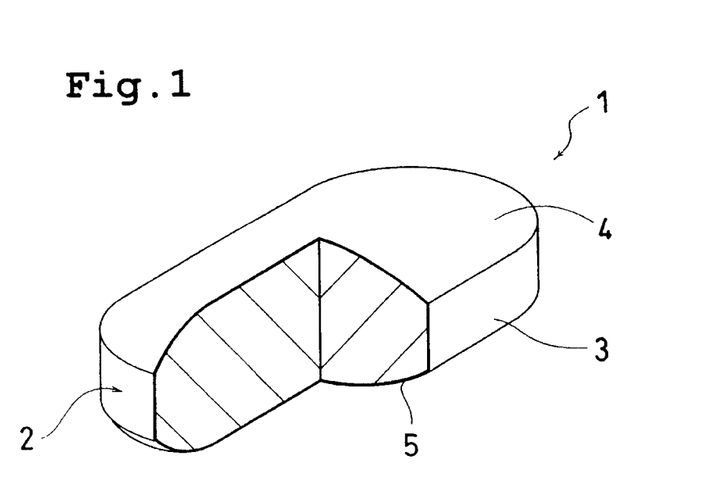
[FIG. 1] is a partly broken perspective view of a tablet showing an embodiment of the present invention.
Figure 2:
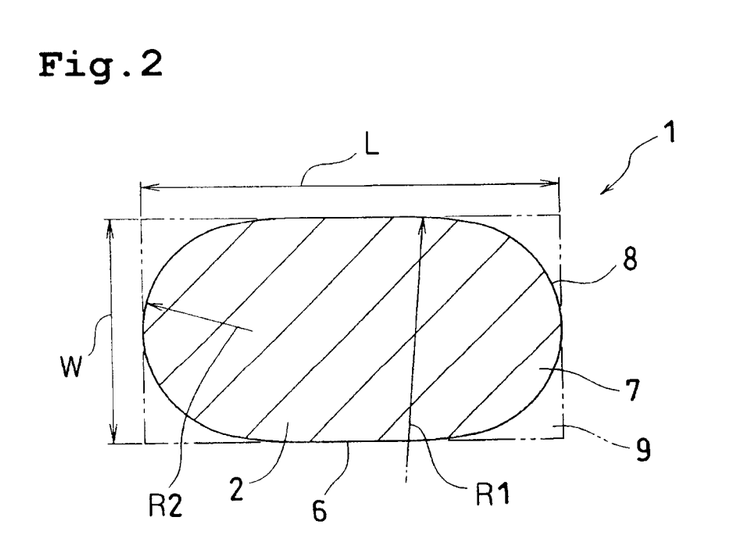
[FIG. 2] is a top view, in cross section, of the tablet according to the embodiment of the present invention.

FIGS. 1 and 2 show embodiments of the present invention. FIG. 1 is a partly broken perspective view and FIG. 2 is a top view, in cross section of a tablet.

As shown in FIG. 1, a tablet 1 has a main body 2 a peripheral side surface 3 of which is formed vertical. The main body 2 is formed at its upper and lower surfaces with projections 4 each of which smoothly protrudes in the shape of an elliptical semi-sphere. A film-coating 5 is applied to the surfaces of this tablet 1. As for the components of this film-coating 5 and the way to carry out the coating treatment, for example, it is possible to adopt the materials and ways used for the general tablets and therefore they are not limited to specific ones. Besides, the components of the tablet 1 itself need not be limited to specific ones. Additionally, the tablet 1 of the present invention may have the peripheral side surface 3 tapered.

As shown in FIG. 2, the table 1 is formed in the shape of a substantial ellipse longer in one direction and has side edges 6 extending along a longitudinal direction, each of which is formed by a curve projecting outwardly in plan view. A radius of curvature (R1) of this curve is set to at least 1.5 times, preferably at least 2 times, and more preferably at least 2.5 times a length (L) of the tablet.

The tablet 1 has end portions 7 each of which is formed by an end arc 8 projecting outwards when seen in in plan. The end arc 8 has a radius of curvature (R2) whose opposite ends are smoothly connected to the side edges 6, respectively. The radius of curvature (R2) of the end arc 8 is smaller than half a width (W) of the tablet. When the end arc 8 is brought into contact with the side edges 6, the radius of curvature is calculated from the tablet width (W), the tablet length (L) and the radius of curvature (R1) of the side edge 6. However, it suffices if the end arc 8 is substantially smoothly connected to the side edges 6 and therefore the radius of curvature (R2) may be slightly larger than the calculated value.

The side edge 6 has the radius of curvature (R1) so set that the projected area of the tablet in plan view comes to be at least 86% with respect to the rectangle 9 having the width (W) and the length (L). Further, this projected area is set to at least 97% with respect to the projected area of the standard elliptical tablet of the same width (W) and the same length (L) having opposite end portions each of which is formed by a semi-circle of the tablet width (W) as a diameter.

EXAMPLES

Hereafter, we will explain the present invention in more detail while listing Examples, Comparison Examples and Test Examples. But the present invention is not limited to those Examples.

In the below-mentioned Examples and Comparison Examples, the agents which satisfy The Japanese Pharmacopoeia Fourteenth Edition or the Japanese Pharmaceutical Excipients 2003 were used for various sorts of additives such as magnesium stearate.

Examples 1 to 7 and Comparison Examples 1 to 5

The length (L), the width (W) of the tablet shown in FIG. 2 are set to various dimensions as well as the radius of curvature (R1) of the side edge 6 and the radius of curvature (R2) of the end arc 8. Then measurements were made for the projected areas of the respective tablets 1 when seen in plan (Examples 1 to 7). The results of the measurement were compared with those of the conventional standard elliptical tablets (Comparison Examples 1 to 3) and oval tablets (Comparison Examples 4 and 5) and were indicated in Table of Comparison of Dimension in FIG. 3.

Figure 3:
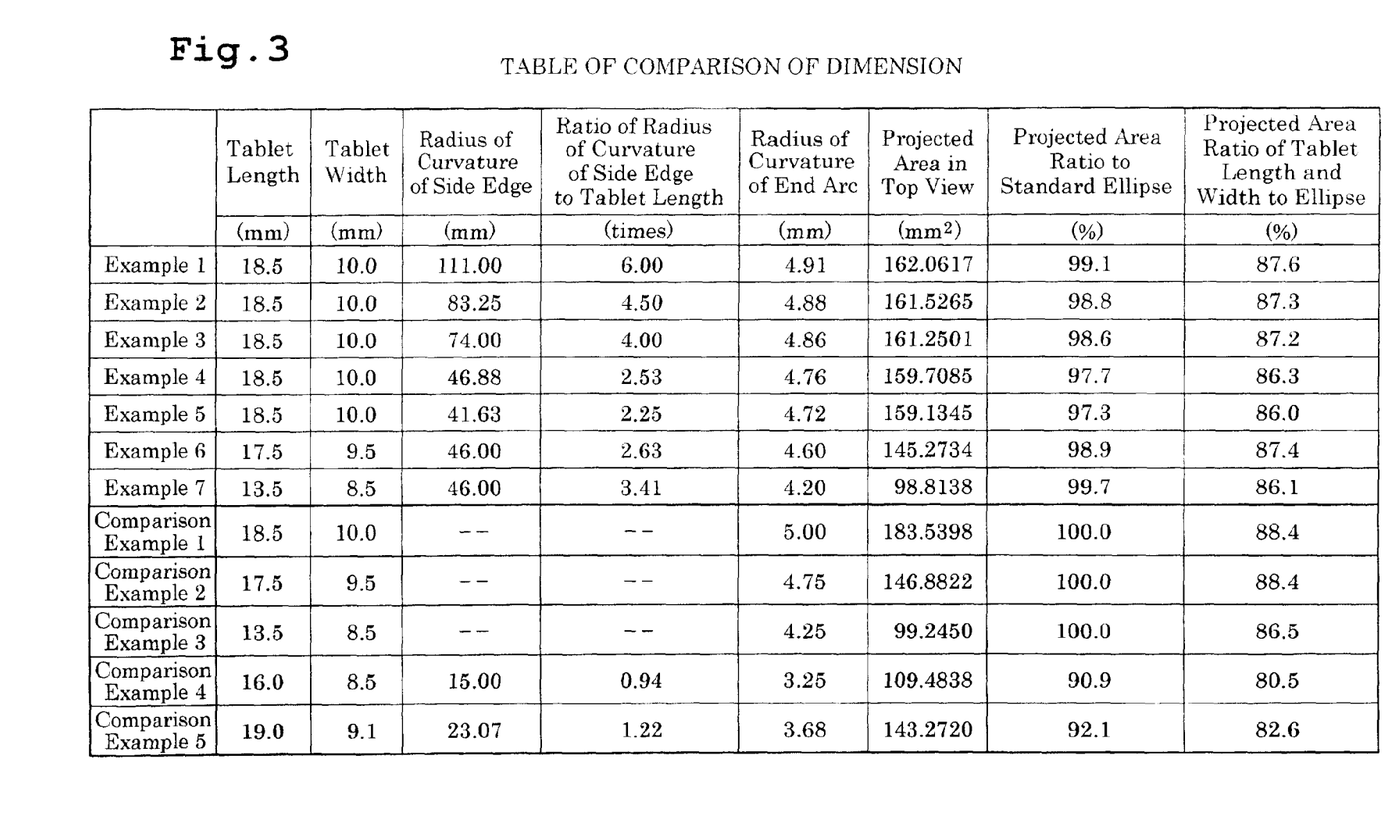
[FIG. 3] is a Table of Comparison of Dimension in which the tablet of the embodiment according to the present invention is compared with that of the prior art in dimension.

As indicated in Table of Comparison of Dimension in FIG. 3, each of the tablets of Examples 1 to 7 has a large projected area ratio of at least 97% with respect to the standard elliptical tablet and therefore could retain its volume large.

On the other hand, each of the tablets (oval tablets) of Comparison Examples 4 and 5 has a narrow projected area in plan view and as a result could not keep its volume large.

Hereafter, we will recite how to produce the tablets of Examples 4, 6 and 7 as well as those of Comparison Examples 1 to 3.

Example 4

57800 g of metoformin hydrochloride, 1147 g of pioglytazon hydrochloride and 2052 g of microcrystalline cellulose were entered into a flow granulating and drying machine (manufactured by POWREX CORPORTION, Model WSG-60) and were granulated while spraying 18700 g of purified water containing 3740 g of polyvinylpyrrolidone to have obtained an intermediate granule through a drying step. The same operation was repeated twice and obtained a granule.

123800 g of the obtained granule was mixed with 8320 g of microcrystalline cellulose, 6587 g of croscarmellose sodium and 429 g of magnesium stearate.

The obtained powder granule was made into tablets by using a tablet-making machine (manufactured by KIKUSUI SEISAKUSHO LTD., AQUA 0836, 18.5 mm×10 mm in dimension of tablet, compression pressure of 27 kN/punch, shape of rod; substantially oval, ratio of radius of curvature of a side edge with respect to the length of a tablet: 2.53) to have obtained tablets each of which weighs 1220 mg.

122600 g of the obtained tablets were thrown into a film-coating device (manufactured by POWREX CORPORTION, DRS-1200DS) to coat them by spraying 35172 g of purified water containing 2227 g of hydroxypropylmethyl cellulose, 430 g of polyethylene glycol 6000, 430 g of titanium oxide and 430 g of talc dispersed, at an inlet temperature of 80 degrees C. in an amount of 200 g/min. Then film-coated tablets, each of which weights 1255 mg, were obtained.

Example 6

20000 g of pioglytazon hydrochloride and 4998 g of microcrystalline cellulose were entered into a mixing machine (manufactured by POWREX CORPORTION, vertical granulator) and were mixed while agitating them. The obtained mixture was crushed by a jet-mill crusher (manufactured by NPK Company, Model 100SP) to have obtained crushed mixture of pioglytazon hydrochloride and microcrystalline cellulose.

85000 g of metoformin hydrochloride, 2107 g of the crushed mixture of pioglytazon hydrochloride and microcrystalline cellulose, and 2637 g of microcrystalline cellulose were entered into a flow granulating and drying machine (manufactured by POWREX CORPORTION, Model STRE-5M) and were granulated while spraying 27500 g of purified water containing 5500 g of polyvinylpyrrolidone to have obtained an intermediate granule through a drying step. The same operation was repeated three times and obtained a granule.

The obtained granule was mixed with 19200 g of microcrystalline cellulose, 15200 g of croscarmellose sodium and 990 g of magnesium stearate.

The obtained powder granule was made into tablets by using a tablet-making machine (manufactured by KIKUSUI SEISAKUSHO LTD., Correct D55, 17.5 mm×9.5 mm in dimension of tablet, compression pressure of 27 kN/punch, shape of rod; substantially oval, ratio of radius of curvature of a side edge with respect to the length of a tablet: 2.63) to have obtained tablets each of which weights 1070 mg.

The obtained tablets were thrown into a film-coating device (manufactured by POWREX CORPORTION, DRS-1600) to coat them by spraying 90000 g of purified water containing 5697 g of hydroxypropylmethyl cellulose, 1100 g of polyethylene glycol 6000, 1100 g of titanium oxide and 1100 g of talc dispersed, at an inlet temperature of 80 degrees C. in an amount of 200 g/min. Then film-coated tablets, each of which weights 1100 mg, were obtained.

Example 7

20000 g of pioglytazon hydrochloride and 4998 g of microcrystalline cellulose were entered into the mixing machine (manufactured by POWREX CORPORTION, vertical granulator) and were mixed while agitating them. The obtained mixture was crushed by a jet-mill crusher (manufactured by NPK Company, Model 100SP) to have obtained crushed mixture of pioglytazon hydrochloride and microcrystalline cellulose.

85000 g of metoformin hydrochloride, 3582 g of the crushed mixture pioglytazon hydrochloride and microcrystalline cellulose, and 2409 g of microcrystalline cellulose were entered into a flow granulating and drying machine (manufactured by POWREX CORPORTION, MODEL STRE-5M) and were granulated while spraying 28050 g of purified water containing 5610 g of polyvinylpyrrolidone to have obtained an intermediate granule through a drying step. The same operation was repeated three times and obtained a granule.

The obtained granule was mixed with 19380 g of microcrystalline cellulose, 15390 g of croscarmellose sodium and 1020 g of magnesium stearate.

The obtained powder mixture was made into tablets by using a tablet-making machine (manufactured by KIKUSUI SEISAKUSHO LTD., Correct, D55, 13.5 mm×8.5 mm in dimension of tablet, compression pressure of 14 kN/punch, shape of rod; substantially oval, ratio of radius of curvature of a side edge with respect to the length of a tablet: 3.41) to have obtained tablets each of which weighs 638 mg.

The obtained tablets were thrown into a film-coating device (manufactured by POWREX CORPORTION, DRS-1600) to coat them by spraying 96900 g of purified water containing 6139 g of hydroxypropylmethyl cellulose, 1183 g of polyethylene glycol 6000, 1183 g of titanium oxide and 1183 g of talc dispersed, at an inlet temperature of 80 degrees C. in an amount of 200 g/min. Then film-coated tablets, each of which weights 657 mg, were obtained.

Comparison Example 1

The powder mixture obtained in Example 4 was made into tablets by using a tablet-making machine (manufactured by KIKUSUI SEISAKUSHO LTD., AQUA 0836, 18.5 mm×10 mm in dimension of tablet, compression pressure of 27 kN/punch, shape of rod; ellipse) to have obtained tablets each of which weights 1220 mg.

The obtained tablets were coated by the same operation as in Example 4 to have obtained film-coated tablets each of which weights 1255 mg.

Comparison Example 2

8430 g of pioglytazon hydrochloride and 2106 g of microcrystalline cellulose were entered into a mixing machine (manufactured by POWREX CORPORTION, vertical granulator) and were mixed while agitating them. The obtained mixture was crushed by the jet-mill crusher (manufactured by NPK Company, Model 100SP) to have obtained crushed mixture of pioglytazon hydrochloride and microcrystalline cellulose.

102000 g of metoformin hydrochloride, 2526 g of the crushed mixture of pioglytazon hydrochloride and microcrystalline cellulose, and 3164 g of microcrystalline cellulose were entered into a flow granulating and drying machine (manufactured by POWREX CORPORTION, MODEL STRE-5M) and were granulated while spraying 33000 g of purified water containing 6600 g of polyvinylpyrrolidone to have obtained a granule through a drying step.

106600 g of the obtained granule was mixed with 7168 g of microcrystalline cellulose, 5675 g of croscarmellose sodium and 369.3 g of magnesium stearate.

The obtained powder mixture was made into tablets by using a tablet-making machine (manufactured by KIKUSUI SEISAKUSHO LTD., AQUA0836, 17.5 mm×9.5 mm in dimension of tablet, compression pressure of 20 kN/punch, shape of rod; ellipse) to have obtained tablets each of which weighs 1070 mg.

108100 g of the obtained tablets were thrown into a film-coating device (manufactured by POWREX CORPORTION, DRS-1200DS) to coat them by spraying 30310 g of purified water containing 1919 g of hydroxypropylmethyl cellulose, 371 g of polyethylene glycol 6000, 371 g of titanium oxide and 371 g of talc dispersed, at an inlet temperature of 80 degrees C. in an amount of 200 g/min. Then film-coated tablets, each of which weights 1100 mg, were obtained Comparison Example 3

8430 g of pioglytazon hydrochloride and 2106 g of microcrystalline cellulose were entered into a mixing machine (manufactured by POWREX CORPORTION, vertical granulator) and were mixed while agitating them. The obtained mixture was crushed by the jet-mill crusher (manufactured by NPK Company, Model 100SP) to have obtained crushed mixture of pioglytazon hydrochloride and microcrystalline cellulose.

93500 g of metoformin hydrochloride, 3936 g of the crushed mixture of pioglytazon hydrochloride and microcrystalline cellulose, and 2650 g of microcrystalline cellulose were entered into a flow granulating and drying machine (manufactured by POWREX CORPORTION, MODEL STRE-5M) and were granulated while spraying 30855 g of purified water containing 6171 g of polyvinylpyrrolidone to have obtained a granule through a drying step.

99370 g of the obtained granule was mixed with 6650 g of microcrystalline cellulose, 5280 g of croscarmellose sodium and 350 g of magnesium stearate.

The obtained powder mixture was made into tablets by using a tablet-making machine (manufactured by KIKUSUI SEISAKUSHO LTD., AQUA0836, 13.5 mm×8.5 mm in dimension of tablet, compression pressure of 14 kN/punch, shape of rod; ellipse) to have obtained tablets each of which weighs 638 mg.

95700 g of the obtained tablets were thrown into a film-coating device (manufactured by POWREX CORPORTION, DRS-1200DS) to coat them by spraying 28500 g of purified water containing 1806 g of hydroxypropylmethyl cellulose, 348 g of polyethylene glycol 6000, 348 g of titanium oxide and 348 g of talc dispersed, at an inlet temperature of 80 degrees C. in an amount of 200 g/min. Then tablets coated with a film of pharmaceutical composition, each of which weights 657 mg, were obtained.

Test Example 1

Twin tablets were selected by an inspection with eyes from among the film-coated tablets obtained in the above-mentioned Examples 4, 6 and 7, and Comparison Examples 1 to 3. The number of occurrence of the twin tablets was divided by the total number of the tablets and the resulting value was expressed in ppm. The results are shown in Table 1.

TABLE 1

Measurement Result of Occurrence
Rate of Twin Tablet

|  | Rate of Occurrence of Twin Tablet (ppm) |
|---|---|
| Example 4 | 0 |
| Example 6 | 0 |
| Example 7 | 0 |
| Comparison Example 1 | 2313 |
| Comparison Example 2 | 110 |
| Comparison Example 3 | 240 |

As indicated in Table 1, as for the film-coated tablets obtained in Examples 4, 6 and 7 (tablets according to the present invention), no twin tablet occurred and therefore the occurrence of twin tablet could be completely inhibited. On the other hand, as to the film-coated tablets of Comparison Example 1 to 3 (standard elliptical tablets), twin tables occurred in each of them. The longer the linear portion of the side edge, the higher the occurrence rate. Particularly, in the case of Comparison Example 1 where the side edge had the longest linear portion, the occurrence rate was 2313 ppm (about 0.23%).

Test Example 2

As regards the film-coated tablets obtained in Example 4 and Comparison Example 1, the thickness and hardness of every tablet were measured. The result of the measurement was shown in Table 2.

TABLE 2

Result of Measurement of the
Thickness and Hardness of Tablet

|  | Thickness (mm) | Hardness (N) |
|---|---|---|
| Example 4 | 7.59-7.64 | 230 |
| Comparison Example 1 | 7.59-7.74 | 237 |

The thickness of tablet: expressed in a range of the values measured individually of 20 tablets.
The hardness of tablet: expressed by average value of 10 tablets.

As shown in Table 2, the thickness and hardness of each of the film-coated tablets (tablets according to the present invention) obtained in Example 4 were identical to those of the film-coated tablets (standard elliptical tablets) obtained in Comparison Example 1. More specifically, since these film-coated tablets are the same in the aspects of the dimension of tablet (width and length of tablet), the compression pressure and the weight, apparently, the tablet of the present invention can retain its volume large without increasing its thickness as well as the standard elliptical tablet.

The tablets explained in the above-mentioned Embodiments and Examples are exemplified for embodying the technical idea of the present invention. Therefore, the length, width and thickness of the tablet are not limited to those of the embodiments but various changes can be added thereto as far as they fall within a scope of claims of the present invention.

For example, in the foregoing Embodiments and Examples, the radius of curvature of the side edge along the longitudinal direction of the tablet is set to at least 1.5 times the length of the tablet and the projected area in plan view is set to at least 97% with respect to the projected area of the standard elliptical tablet. Accordingly, this is preferable because it is possible to retain the volume large without increasing the thickness or the like dimension of the tablet.

However, the relationship between the radius of curvature of the side edge and the ratio of the projected area to the standard elliptical tablet differs depending on the ratio of the tablet length to the tablet width. When the tablet is short, even if the radius of curvature is small, the ratio of the projected area can be set to a large one. Therefore, according to the present invention, if the projected area in plan is set to at least 97% with respect to the projected area of the standard elliptical tablet, the radius of curvature of the side edge may be below 1.5 times the length of the tablet.

On the contrary, in the case of a longer tablet, the projected area itself of the standard elliptical tablet occupies large ratio with respect to a rectangle having the tablet width and length. In consequence, according to the present invention, if the radius of curvature of the side edge is set to at least 1.5 times the length of the tablet, the projected area can be increased with respect to the rectangle having the tablet width and length. Accordingly, since it is possible to retain the volume large without increasing the thickness of the tablet or the like dimension, the projected area in plan view may be below 97% with respect to the projected area of the standard elliptical tablet.

Further, although the explanation was made for the tablets each having a smooth surface in the respective embodiments, the shape of the surface of the tablet is not limited to a specific one but the tablet may be a divisible one formed with a dividing groove in its surface as well as the above-mentioned conventional technique. Besides, the tablet of the present invention may be printed with a carved seal or a word for distinguishing purpose.

INDUSTRIAL AVAILABILITY

The present invention is suitable particularly for the film-coated tablet because the volume of the tablet can be kept large without increasing the thickness of the tablet or the like dimension and a plurality of tablets car be inhibited from sticking to each other even if they are subjected to a film-coating or the like treatment so as to improve the yield, but, needless to say, it is applicable to other tablets.

The invention claimed is:
1. A tablet comprising a pharmaceutical active component and/or a therapeutic agent in a quantity dosed for swallowing,
   wherein the tablet has a main body with upper and lower surfaces that each smoothly protrude outwardly in a shape of an elliptical semi-sphere,
   wherein the tablet has a peripheral side surface that extends vertically between a peripheral edge of the upper surface and a peripheral edge of the lower surface,
   wherein, when the tablet is viewed in a plan of the upper surface:
      the tablet has a length that is greater than a width;
      the tablet has opposing peripheral side portions that extend along a portion of the length of the tablet;
      the opposing peripheral side portions each define an outwardly projecting curve having a radius of curvature at least 2.53 times a length of the tablet but not more than 3.41 times the length of the tablet;

the tablet has opposing peripheral end portions that each define an outwardly projecting end arc having a radius of curvature that is smaller than half a width of the tablet; and the tablet has a projected area in the plan view of at least 97% with respect to a projected area of an object having the same length and width as the tablet but having opposing linear peripheral side edges and opposite peripheral end portions that each define a semi-circle having a diameter equal to the width of the tablet; and wherein the tablet is provided with a film-coating.

2. The tablet as set forth in claim 1, wherein, when the tablet is viewed in the plan of the upper surface, the peripheral edge of the upper surface is outwardly curved in its entirety.

3. The tablet as set forth in claim 1, wherein the end arcs of the opposing end portions have opposite ends that smoothly connect to the opposing peripheral side portions of the tablet.

4. The tablet according to claim 1, wherein the film-coating is 10 to 200 μm thick.

5. The tablet according to claim 1, wherein the tablet weighs at least 150 mg.

6. The tablet according to claim 1, wherein the tablet weighs at least 300 mg.

7. The tablet according to claim 1, wherein the tablet weighs at least 600 mg.

\* \* \* \* \*